United States Patent [19]
Wendt et al.

[11] 3,935,191
[45] Jan. 27, 1976

[54] AMINOALKYL ETHERS OF 2,2'- AND 3,3'-DIHYDROXYBENZIL

[75] Inventors: Gerhard R. Wendt, Havertown; Michael W. Winkley, Malvern, both of Pa.

[73] Assignee: American Home Products Corporation, New York, N.Y.

[22] Filed: Oct. 9, 1974

[21] Appl. No.: 513,354

[52] U.S. Cl. . 260/239 B; 260/239 BA; 260/293.64; 260/326.5 G; 260/570 R; 424/244; 424/267; 424/274; 424/325
[51] Int. Cl.² ....................................... C07D 295/08

[56] References Cited
UNITED STATES PATENTS
3,718,643   2/1973   Fried ............................ 260/326.5 G Primary Examiner—Alton D. Rollins
Assistant Examiner—Mark L. Berch
Attorney, Agent, or Firm—David E. Frankhouser

[57] ABSTRACT

Dialkylaminoalkyl ethers of 2,2'- and 3,3'-dihydroxybenzil are prepared by reacting the dithallium salt of 2,2'- or 3,3'-dihydroxybenzil with a dialkylaminoalkylchlorde. The products have antiarrhythmic activity.

13 Claims, No Drawings

AMINOALKYL ETHERS OF 2,2'- AND 3,3'-DIHYDROXYBENZIL

This invention relates to chemical compounds classified in the art of organic chemistry as aminoalkylethers of 2,2'- and 3,3'-dihydroxybenzil having useful pharmacological activity. The compound 5,5'-dichloro-2,2'-bis(2-diethylaminoethoxy)benzil is described by J. Finkelstein and S. M. Linder, *J. Amer. Chem. Soc.*, 71, 1010 (1949).

The invention sought to be patented comprises compounds having the molecular formula:

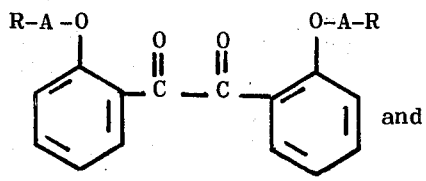

I

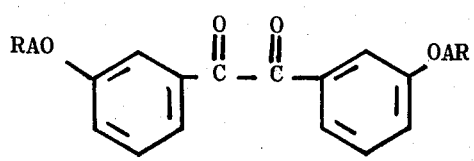

II wherein A is a divalent aliphatic hydrocarbon radical of the formula

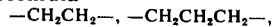

or

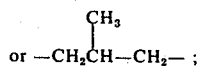

and R is a substituted amino group of the formula

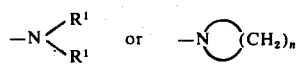

wherein $R^1$ is methyl, ethyl, propyl, or isopropyl, and n is the number 4, 5, or 6; and the non-toxic, pharmaceutically acceptable acid addition salts thereof.

The compounds of Formula I and II in standard pharmacolgical test procedures elevate the electrical fibrillatory threshold of anesthetized dogs evidencing usefulness as antiarrhythmic agents. In addition, the compounds inhibit ADP-induced blood platelet aggregation indicating usefulness as antithrombitic agents.

The compounds of Formula I and II are prepared by condensing a dithallium salt of 2,2'-dihydroxybenzil or 3,3'-dihydroxybenzil with an appropriate di(substituted)aminoalkylchloride in refluxing toluene or toluene-dimethylformamide. The compounds obtained in the free base form can be conveniently isolated and purified in the form of an acid addition salt. Such salts are made by conventional methods such as by combining the base and a suitable acid in a reaction-inert organic solvent.

The dithallium salts are prepared by reaction of 2,2'- or 3,3'-dihydroxybenzil with thallium (I) ethoxide in an inert organic solvent, for example, benzene, toluene, or ethanol-benzene. The salt precipitates from the reaction medium and can be isolated by filtration. [See Taylor et al., *J. Am. Chem. Soc.*, 90, 245 (1968) and Paquet et al., *Can. J. Chem.*, 51, 3855 (1973)].

For pharmacological purposes the compounds can be employed in the form of acid addition salts with non-toxic and pharmaceutically acceptable acids. Such acids will be apparent to one skilled in the art. Appropriate salts are those formed from either inorganic or organic acids, for example, hydrochloric, hydrobromic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, benzenesulfonic, p-toluenesulfonic, and 2-naphthalenesulfonic.

The methods of making and using the compounds of the invention are illustrated in the following examples:

EXAMPLE 1

2,2'-Bis-(2-Diethylaminoethoxy)Benzil

A suspension of 30 g. (0.046M) of 2,2'-dihydroxybenzil dithallium salt in 648 ml. of dry toluene was stirred vigorously and heated (oil bath) to reflux while adding a solution of 15 g. (0.11M) of previously distilled diethylamino ethyl chloride in 130 ml. of dry toluene. Stirring and refluxing were continued for 8½ hours. After cooling the mixture, the pale yellow solid was filtered off and washed with ether. The filtrate was evaporated to dryness to obtain 23 g. of oily material which began to crystallize on standing at 25°.

The material was dissolved in 250 ml. of ether and acidified to pH 1 with 4N isopropanolic HCl. The resulting white precipitate was diluted to 400 ml. with ether and stored at +5° for a few hours. The solid material was then collected by filtration, washed with ether and sucked dry. Recrystallization from 100 ml. of methanol and 200 ml. of ether afforded 21.3 g. of the title compound as the dihydrochloride salt; m.p. 243°–244°; $\lambda_{max}^{KBr}$ 2.96, 3.45, 3.85, 4.10, 5.99, 6.25, 6.75, 6.88 μ.

Analysis for: $C_{26}H_{38}O_4N_2Cl_2$. Calculated: C, 60.81; H, 7.46; N, 5.46; Cl, 13.81 %. Found: C, 60.37; H, 7.48; N, 5.76; Cl, 14.04.

EXAMPLE 2

2,2'-Bis(3-dimethylaminopropoxy)Benzil

A suspension of 15 g. (0.023 M) of 2,2'-dihydroxybenzil dithallium salt in 500 ml. of dry toluene was stirred vigorously at 25° and a solution of 6.1 g. (0.05 M) of 3-dimethylaminopropyl chloride in 61 ml. of toluene was added dropwise as the mixture was gradually heated to reflux (maximum oil bath heat was 150°). After stirring and refluxing for 12 hours, the reaction mixture was cooled to 25° and the still yellow suspension was gradually heated to reflux again while adding an additional 6.1 g. (0.05 M) of 3-dimethylaminopropyl chloride. After stirring and refluxing for 4-5 more hours, the suspension was practically colorless. The mixture was cooled to 25°, and the suspended material, filtered off and washed with toluene. The filtrate from the above filtration was washed with 10% sodium hydroxide, saturated brine solution, and finally dried over $MgSO_4$.

Evaporation of the dry toluene extract resulted in an oily residue which was dissolved in 100 ml. of ether and acidified with 4N isopropanolic HCl. The resulting gum obtained was crystallized from methanol-ether. After recrystallization from 50 ml. of methanol and 100 ml. of ether, 7.0 g. of crystalline material was obtained and identified to be the title compound as the dihydrochloride salt; m.p. 211°–214°; $\lambda_{max}^{KBr}$ 4.10, 5.95, 6.05, 6.22 $\mu$; NMR 2.05 (s), 7.1–8.2 (m) ppm.

Analysis for: $C_{24}H_{32}N_2O_4 \cdot 2HCl$. Calculated: C, 59,38; H, 7.06; N, 5.77; Cl, 14.61 %. Found: C, 59.60; H, 7.16; N, 5.76; Cl, 14.92.

EXAMPLE 3

2,2'-Bis(3-Dimethylamino-2-Methylpropoxy)Benzil

A suspension of 15 g. (0.023 M) of 2,2'-dihydroxybenzil dithallium salt in 500 ml. of dry toluene was stirred vigorously while adding dropwise a solution of 8.8 g. (0.05 M) of 3-dimethylamino-2-methyl propyl chloride in 91.5 ml. of toluene. The mixture was gradually heated to reflux during the addition, and the resulting mixture was stirred and refluxed for 12 hours before a color change was observed. After cooling to 25°, the pale yellow solid was filtered off and washed with toluene. The material was resuspended in toluene and filtered off again. The combined filtrates were washed with 10% sodium hydroxide solution, saturated brine solution, and finally dried over $MgSO_4$. Evaporation of the dry toluene extract with heating up to 70° at 11 mm resulted in an oily residue. Various salts were prepared but failed to solidify. The free base was regenerated and the crude material began to crystallize. The product was recrystallized from hexane. After cooling to +5° overnight, the material was filtered off and dried in vacuo over $P_2O_5$ and paraffin wax to obtain 3.8 g. of the title compound; m.p. 69°–70°; $\lambda_{max}^{KBr}$ 3.55, 5.88, 6.10, 6.55, 6.72 $\mu$.

Analysis for: $C_{26}H_{36}N_2O_4$. Calculated: C, 70.88; H, 8.24; N, 6.36 %. Found: C, 70.99; H, 8.42; N, 6.31.

EXAMPLE 4

2,2'-Bis(2-Diisopropylaminoethoxy)Benzil

A solution of diisopropylaminoethyl chloride (166 ml. of 24 g./250 ml.) in toluene was added to a stirred dry suspension of 2,2'-dihydroxybenzil dithallium salt (26 g.) in toluene (900 ml.) and the mixture was stirred and heated under reflux for 3½ hrs. The mixture was cooled and filtered. The filter pad was washed with toluene and the filtrate and washings were evaporated to dryness under oil pump vacuum. The resulting solid was dissolved in ether and the solution was filtered through Celite. The solution was evaporated and the resulting solid was triturated with ether to give 17.66 g.; m.p. 83°–87°.

A portion (15.0 g.) of the above amine was dissolved in ether and the solution was cooled in ice. Dry hydrogen chloride was blown into the solution. The solid was collected and recrystallized from methanol-ether to give 16.84 g.; m.p. 243°–245° dec. of title product as the dihydrochloride salt. Recrystallization from methanol-ether gave material; m.p. 246°–248° dec.

Analysis for: $C_{30}H_{46}Cl_2N_2O_4$ Calculated: C, 63.25; H, 8.14; Cl, 12.45; N, 4.92 %. Found: C, 63.34; H, 8.16; Cl, 12.75; N, 5.26.

EXAMPLE 5

3,3'-Bis(2-Diethylaminoethoxy)Benzil

A dry suspension of 3.0 g. (4.6 mM) of dry 3,3'-dihydroxybenzil dithallium salt in 70 ml. of dry toluene was stirred and heated to reflux while treating with a solution 1.5 g. (11 mM) of freshly distilled diethylamino ethyl chloride in 10 ml. of dry toluene. The suspension was stirred and refluxed for 4 hours. After cooling, the insoluble material was removed by filtration and the filtrate was distilled to obtain 2.0 g. of oil (99% of theory).

A solution of 1.0 g. (2.3 mM) of the oil in 5 ml. of absolute alcohol was added to a solution of 1.1 g. (6 mM) of p-toluenesulfonic acid in 10 ml. of absolute alcohol. The alcoholic solution was diluted to 175 ml. with ether, and the resulting precipitate collected by filtration. Recrystallization from 5 ml. of methanol plus 5 ml. of ether afforded 1.2 g. (67.5%) of material identified to be the title compound as the bis(p-toluenesulfonate) salt; m.p. 134°–137°; $\lambda_{max}^{KBr}$ 3.40, 3.76, 5.95, 6.01, 6.25 $\mu$.

Analysis for: $C_{40}H_{52}N_2O_{10}S_2$. Calculated: C, 61.30; H, 6.68; N, 3.56; S, 8.17 %. Found: C, 61.03; H, 6.43; N, 3.78; S, 7.96.

EXAMPLE 6

3,3'-Bis(3-dimethylaminopropoxy)Benzil

A suspension of 20 g. (0.031 M) of 3,3'-dihydroxybenzil dithallium salt, in 500 ml. of dry toluene was stirred at 25° while adding 9 g. (0.074 M) of 3-dimethylamino propyl chloride in 90 ml. of toluene. The mixture was gradually heated to boiling and refluxed for 5 hours. After cooling to 25°, the brown suspension was removed by filtration and the filtrate was evaporated to dryness to obtain a gummy residue which was dissolved in 50 ml. of alcohol and added to a solution of 7.25 g. (0.038 M) of p-toluenesulfonic acid in 35 ml. of alcohol. The resulting solution was diluted to 100 ml. with ether resulting in a solid mass of precipitate. The material was collected by filtration, washed with ether, and air dried. After recrystallizing once from 50 ml. of methanol and 25 ml. of ether and finally from 50 ml. of alcohol, 8.1 g. of product was obtained and identified to be the title compound as the bis(p-toluenesulfonate) salt; m.p. 168°–170°; $\lambda_{max}^{KBr}$ 3.05, 5.98, 6.25, 6.73, 6.93 $\mu$.

Analysis for: for: $C_{38}H_{48}N_2O_{10}S_2$. Calculated: C, 60.30; H, 6.39; N, 3.70; S, 8.47 %. Found: C, 60.20; H, 6.41; N, 3.34; S, 8.42.

EXAMPLE 7

3,3'-Bis(3-Dimethylamino-2-methylpropoxy)Benzil

To a dry, stirred suspension of 3,3'-dihydroxybenzil dithallium salt (20 g.) in toluene (250 ml.) and N,N-dimethylformamide (250 ml.) was added dropwise 104 ml. of a solution containing 48 g. of 3-dimethylamino-2-methylpropyl chloride in 500 ml. of toluene. The mixture was stirred and heated under reflux overnight. The resulting heavy white precipitate was removed and washed with toluene. The toluene solution and washings were evaporated to a syrup which was subjected to further evaporation using an oil pump vacuum. The syrup was dissolved in chloroform and applied to a column (48 × 5.2 cm) of a "dry column grade" alumina (Woelm) prepacked in chloroform. Elution was with chloroform and 500 ml. fractions (1 and 2) and 250 ml. (3–6) fractions were collected. Fractions 3–6 were pooled and evaporated to give 10.00 g. of syrup. To 7.55 g. of this material in ethanol (150 ml.) was added naphthalene-2-sulfonic acid (7.72 g.). The solution was warmed and decolorized. Evaporation and addition of seeds and ether gave the title product (9.88 g.) as the bis(2-naphthalenesulfonate) salt; m.p. 162-164°. Recrystallization with decolorization gave pure product; m.p. 164-166°.

Analysis for: $C_{46}H_{52}N_2O_{10}S_2$ Calculated: C, 64.46; H, 6.12; N, 3.27; S, 7.48 %. Found: C, 64.89; H, 6.21; N, 3.16; S, 7.54.

EXAMPLE 8

3,3'-Bis(2-Diisopropylaminoethoxy)Benzil

To a dried stirred suspension of 3,3'-dihydroxybenzil dithallium salt (10 g.) in toluene (250 ml.) was added dropwise 65 ml. of a solution containing 25 g. of diisopropylaminoethyl chloride in 250 ml. of toluene. The mixture was stirred and heated under reflux for 1½ hours. The white precipitate was removed and washed with benzene. The solution and washings were evaporated to dryness. The syrup was dissolved in chloroform and added to a column (45 × 5.3 cm) of "Dry-Column Grade" alumina (Woelm) prepacked in chloroform. The column was eluted with chloroform and 200 ml. fractions were collected. Fractions 5-9, which contained a single component as judged by tlc on Alox-25 UV 254 (Brinkmann) plates with chloroform as developer, were pooled and evaporated to give 6.09 g. of a syrup.

This material was dissolved in ethanol (50 ml.) and p-toluenesulfonic acid (4.59 g.) was added. Warming followed by cooling and seeding gave 8.22 g. of the title compound as the bis(p-toluenesulfonate)salt; m.p. 157°-159°. Recrystallization with decolorization from ethanol-ether gave pure product; m.p. 158°-160°.

Analysis for: $C_{44}H_{60}N_2O_{10}S_2$. Calculated: C, 62.83; H, 7.17; N, 3.33; S, 7.62 %. Found: C, 63.11; H, 7.22; N, 3.32; S, 7.66.

EXAMPLE 9

2,2'-Bis(2-Piperidinoethoxy)Benzil

To a stirred dry suspension of 2,2'-dihydroxybenzil dithallium salt (20 g.) in toluene (500 ml.) was added dropwise 65 ml. of a solution of N-(2-chloroethyl)-piperidine (79.6 g.) in toluene (500 ml.). The mixture was heated and stirred under reflux for 5 hours. After cooling the precipitate was collected by filtration and washed with toluene. The filtrate and washings were evaporated to a syrup, which was further evaporated under oil pump vacuum. The residual syrup was dissolved in ether and gaseous hydrogen chloride was blown into the cooled solution. The precipitate was crystallized from methanol-ether to give 16.00 g. of title product as the dihydrochloride salt; m.p. 256°-258°.

Analysis For: $C_{28}H_{38}Cl_2N_2O_4$. Calculated: C, 62.57; H, 7.13; Cl, 13.19; N, 5.21 %. Found: C, 62.39; H, 7.43; Cl, 13.16; N, 5.24.

EXAMPLE 10

2,2'-Bis(2-Hexamethyleniminoethoxy)Benzil

To a stirred dry suspension of 2,2'-dihydroxybenzil dithallium salt (30 g.) in toluene (1 liter) was added dropwise 107 ml. of a solution of N-(2-chloroethyl)-hexamethyleneimine (77 g.) in toluene (500 ml.). The mixture was heated and stirred under reflux for 5 hours. After cooling, the precipitate was collected by filtration and washed with toluene. The filtrate and washings were evaporated to a syrup which was further evaporated under oil pump vacuum. The residue was dissolved in chloroform and the solution was added to the top of a column (5.0 × 56 cm) of alumina (Woelm dry-column grade) prepacked in chloroform. The column was eluted with chloroform and 400 ml. fractions were collected. Fractions 4-10, which were homogeneous by tlc on "ALOX-25 UV 254" plates with ethyl acetate as developer, were evaporated to give a syrup (21 g.). To a portion (20.4 g.) dissolved in a minimum volume of ethanol was added 2-naphthalenesulfonic acid hydrate (18.82 g.). The solution was evaporated to smaller volume and seeded. Ether was added to produce crude product. Two recrystallizations from ethanol-ether gave 25.44 g. of the title product as the bis(2-naphthalenesulfonate)salt; m.p. 182°-184°.

Analysis For: $C_{50}H_{56}N_2O_{10}S_2$. Calculated: C, 66.06; H, 6.21; N, 3.08; S, 7.05 %. Found: C, 66.25; H, 6.51; N, 2.99; S, 7.32.

EXAMPLE 11

2,2'-Bis(3-piperidinopropoxy)Benzil

To a stirred dry suspension of 2,2'-dihydroxybenzil dithallium salt (15 g.) in toluene (300 ml.) was added dropwise 51 ml. of a solution of N-(3-chloropropyl)-piperidine (79.5 g.) in toluene (500 ml.). The mixture was heated and stirred under reflux for 5 hours. After cooling the precipitate was collected by filtration and washed with toluene. The filtrate and washings were evaporated to a syrup, which was further evaporated under oil pump vacuum. The residual syrup was dissolved in ether and gaseous hydrogen chloride was blown into the cooled solution. The precipitate was collected and crystallized from methanol-ether to give 13.29 g. of title product as the dihydrochloride salt; m.p. 256°-257° dec.

Analysis For: $C_{30}H_{42}Cl_2N_2O_4$ Calculated: C, 63.71; H, 7.49; Cl, 12.54; N, 4.95. Found: C, 63.43; H, 7.44; Cl, 12.48; N, 4.96.

EXAMPLE 12

2,2'-Bis[2-(3-Azabicyclo[3.2.2]Nonan-3-yl)Ethoxy]-Benzil

To a stirred dry suspension of 2,2'-dihydroxybenzil dithallium salt (20 g.) in toluene (1 liter) was added dropwise 71 ml. of a solution of N-(2-chloroethyl)-3-azabicyclo[3.2.2]nonane (85 g.) in toluene (500 ml.). After the mixture had been stirred and heated under reflux for 2½ hours a further 20 ml. of the reagent was added and stirring and heating were then continued for a further ½ hour. After cooling the precipitate was collected by filtration and washed with toluene. The filtrate and washings were evaporated to syrup which was evaporated further under oil pump vacuum. The residual syrup was dissolved in ether and gaseous hydrogen chloride was blown into the cooled solution to give 23.67 g. of crude product, m.p. 200°-220°. Recrystallization did not give an improved m.p. and, therefore, the base was regenerated by dissolving the crude hydrochloride in a mixture of shaking ice cold 2N sodium hydroxide solution and ether. The ether layer was dried over magnesium sulfate and evaporated to give a solid. Trituration with heptane give 14.67 g. of crude base, m.p. 129°-132°. This product was dissolved in chloroformether and gaseous hydrogen chloride was blown into the cooled solution; yield of title compound 19.31 g.; m.p. 203-207°. Recrystallization from methanol-ethanol-ether gave pure product; m.p. 205°-208°.

Analysis for: $C_{34}H_{46}Cl_2N_2O_4 \cdot 0.5\ H_2O$ Calculated: C, 65.17; H, 7.56; Cl, 11.32; N, 4.47%. Found: C, 65.43; H, 7.57; Cl, 11.62; N, 4.47.

EXAMPLE 13

2,2'-Bis-(2-Pyrrolidinoethoxy)Benzil

To a stirred dry suspension of 2,2'-dihydroxybenzil dithallium salt (26 g.) in toluene (1 liter) was added dropwise 40 ml. of a solution of N-(2-chloroethyl)pyrrolidine (155 g.) in toluene (500 ml.). After the mixture had been stirred and heated under reflux for 1 hour, 20 ml. of reagent solution was added, and after 8 hours, N,N-dimethylformamide (350 ml.) and a further 20 ml. of reagent solution was added. Stirring and heating under reflux were continued for a total of 9 hours. After cooling the precipitate was collected and washed with toluene. The filtrate and washings were evaporated to a syrup which was subjected to an oil pump vacuum. The syrup crystallized on standing. Trituration with hexane gave crystals (16.55 g., m.p. 93°–96°). This material was dissolved in ethanol and p-toluenesulfonic acid hydrate (15.5 g.) was added to the solution. Addition of ether yielded 27.76 g. of title product as the bis(p-toluenesulfonate) salt; m.p. 195°–197°. Recrystallization from methanol-ethanol-ether gave pure product; m.p. 197°–199°.

Analysis for: $C_{40}H_{48}N_2S_2O_{10}$ Calculated: C, 61.52; H, 6.20; N, 3.59; S, 8.21 %. Found: C, 61.67; H, 6.21; N, 3.18; S, 8.29.

EXAMPLE 14

3,3'-Bis(2-Piperidinoethoxy)Benzil

To a stirred dry suspension of 3,3'-dihydroxybenzil dithallium salt (25 g.) in toluene (500 ml.) was added 81 ml. of a solution of N-(2-chloroethyl)piperidine (79.6 g.) in toluene (500 ml.). The mixture was stirred and heated under reflux for 5 hours. After cooling the precipitate was collected and washed with toluene. The filtrate and washings were evaporated to a syrup which was subjected to an oil pump vacuum; yield 18.1 g.

To 17.7 g. of this syrup in ethanol (200 ml.) was added 2-naphthalene sulfonic acid hydrate (17.7 g.). Ether was added and the crystalline product was collected; Yield 26.63 g. of title product as the bis(2-naphthalenesulfonate) salt; m.p. 209°–211°. The product was recrystallized from methanol-ether to give pure products; m.p. 213°–214°.

Analysis for: $C_{48}H_{52}N_2O_{10}S_2$. Calculated: C, 65.43; H, 5.95; N, 3.18; S, 7.28 %. Found: C, 65.17; H, 5.95; N, 2.88; S, 7.37.

EXAMPLE 15

3,3'-Bis(3-Piperidinopropoxy)Benzil

To a stirred dry suspension of 3,3'-dihydroxybenzil dithallium salt (20 g.) in toluene (500 ml.) was added 68 ml. of a solution of N-(3-chloropropyl)piperidine (79.5 g.) in toluene (500 ml.). The mixture was heated and stirred under reflux overnight. After cooling, the precipitate was removed by filtration and washed with toluene. The filtrate and washings were evaporated to a syrup which was further evaporated under oil pump vacuum. The residual syrup was dissolved in ether and gaseous hydrogen chloride was blown into the cooled solution. Recrystallization of the resulting precipitate from methanol-ether gave 17.28 g. of crude product; m.p. 139°–144°. This crude product was shaken with 2N sodium hydroxide and ether and the ether layer was dried ($MgSO_4$) and evaporated to a syrup. The syrup was dissolved in chloroform and the solution was applied to a column (57 × 5.0 cm) of alumina (Woelm, dry-column grade) prepacked in chloroform. The column was eluted with chloroform and 500 ml. fractions were collected. The fractionation was monitored visually. Appropriate fractions were pooled and evaporated to a syrup which was subjected to an oil pump vacuum. The residue was extracted with ether and gaseous hydrogen chloride was blow into the cooled solution. The resulting precipitate was crystallized from methanol-ether to give the title product as the dihydrochloride,hydrate, salt; m.p. 152°–154°.

Analysis for: $C_{30}H_{40}Cl_2N_2O_4 \cdot H_2O$. Calculated: C, 61.74; H, 7.60; Cl, 12.15; N, 4.80 %. Found: C, 62.06; H, 7.58; Cl, 12.31; N, 4.76.

EXAMPLE 16

3,3'-Bis(2-Hexamethyleniminoethoxy)Benzil

To a stirred dry suspension of 3,3'-dihydroxybenzil dithallium salt (30 g.) in toluene (1 liter) was added 107 ml. of a solution of N-(2-chloroethyl)hexamethylenimine(77 g.) in toluene (500 ml.). The mixture was heated and stirred under reflux for 6 hours. After cooling the precipitate was removed by filtration hand washed with toluene. The filtrate and washings were evaporated to a syrup which was subjected to an oil pump vacuum. This material (23.0 g.) was dissolved in ethanol (300 ml.) and 2-naphthalenesulfonic acid hydrate (21.2 g.) was added. The resulting crude crystalline salt (32.09 g.; m.p. 208°–211°) was crystallized twice from N,N-dimethylformamide-ether to give pure title product as the bis(p-naphthalenesulfonate,-hemihydrate) salt; m.p. 216°–218°.

Analysis for: $C_{50}H_{56}N_2O_{10}S_2 \cdot 0.5\ H_2O$. Calculated: C, 65.41; H, 6.26; N, 3.05; S, 6.98; $H_2O$, 0.98 %. Found: C, 65.06; H, 6.45; N, 3.33; S, 6.84; $H_2O$, 0.71.

EXAMPLE 17

3,3'-Bis[3-(3-Azabicyclo[3.2.2]Nonan-3-yl)-Propoxy]Benzil

To a stirred dry suspension of 3,3'-dihydroxybenzil dithallium salt (20 g.) in toluene (1 liter) was added 65 ml. of a solution of N-(2-chloropropyl)-3-azabicyclo[3.2.2]nonane (102 g.) in toluene (500 ml.). After the mixture had been stirred and heated under reflux for ¾ hour, N,N-dimethylformamide (200 ml.) was added, and after 1¼ hours, an additional 30 ml. of reagent solution was added. Stirring and heating under reflux were continued for a total of 5 hours. After cooling the precipitate was collected and washed with toluene. The filtrate and washings were evaporated to an oil. The oil was dissolved in benzene and applied to a column (51 × 5.0 cm) of alumina (Woelm, dry-column grade) prepacked in benzene. The column was eluted with benzene and 100 ml. fractions were collected. At fraction 32 the eluting solvent was changed to chloroform. Fractions 18–48 were pooled and evaporated to a syrup. This syrup was dissolved in ether and hydrogen chloride saturated ether solution was added. The resulting yellow solid (8.47 g.; m.p. 245°–255°) was crystallized twice from methanol-ether to give pure title product as the dihydrochloride salt; m.p. 256°–259°.

Analysis for: $C_{38}H_{50}Cl_2N_2O_4$. Calculated: C, 66.96; H, 7.81; Cl, 10.98; N, 4.34 %. Found: C, 66.81; H, 7.91; Cl, 10.61; N, 4.09.

EXAMPLE 18

3,3'-Bis(3-Pyrrolidinopropoxy)Benzil

To a stirred dry suspension of 3,3'-dihydroxybenzil dithallium salt (25 g., 0.0385 mole) in toluene (500 ml.) was added 3-chloropropylpyrrolidine in toluene (115 ml., 0.09 mole) (30 g. in 250 ml. solution). After three hours of refluxing, dimethylformamide (100 ml.) was added, then the reaction solution was refluxed for another hour. By the end of the reaction, the yellow suspension had turned to off-white color. The filtrate of the reaction suspension was evaporated to dryness (DMF b.p. 150°C) under oil pump vacuum (3-chloropropylpyrrolidine, b.p. 40° C/0.4 mm). The residue was dissolved in chloroform and applied to a column (35.5 × 3.8 cm) of "Dry-Column Grade" alumina (Woelm) prepacked in chloroform. The product was eluted with ethyl acetate. Appropriate fractions were collected and evaporated to smaller volume. A solution of hydrogen chloride in ether was added to the ethyl acetate solution to precipitate the crude dihydrochloride salt. Three crystallizations from methanol-ether gave 9.0 g. (41%) of the title product as the dihydrochloride salt; m.p. 136°–139°.

Analysis for: $C_{28}H_{38}Cl_2N_2O_4$. Calculated: C, 62.58; H, 7.12; N, 5.21; Cl, 13.19 %. Found: C, 62.88; H, 7.41; N, 5.16; Cl, 13.11.

EXAMPLE 19

3,3'-Bis(3-Hexamethyleniminopropoxy)Benzil

To a stirred dry suspension of 3,3'-dihydroxybenzil dithallium salt (25 g., 0.0385 mole) in toluene (500 ml.) was added 3-chloropropylhexamethylenimine in toluene (70 ml., 0.1 mole) (66 g. in 250 ml. solution). After three hours of refluxing, dimethylformamide (100 ml.) was added then the reaction solution was refluxed for another hour. By the end of the reaction, the yellow suspension had turned to off-white. The filtrate of the reaction suspension was evaporated to dryness (DMF b.p. 150°C) under oil pump vacuum (3-chloropropylhexamethylenimine, b.p. 75°C/3.12 mm). The residue was dissolved in chloroform and applied to a column (35.5 × 3.8 cm) of "Dry-Column Grade" alumina (Woelm) prepacked in chloroform. The product was eluted with chloroform. Appropriate fractions were collected and evaporated to a syrup. To a solution of this syrup in methanol was added a solution of hydrogen chloride in ether. The resulting crystalline precipitate was crystallized three times from methanol-ether to give 9.5 g. (42%) of the title product; m.p. 170°–173°.

Analysis for: $C_{32}H_{46}Cl_2N_2O_4$ Calculated: C, 64.74; H, 7.81; Cl, 11.95; N, 4.72 %. Found: C, 64.50; H, 8.07; Cl, 12.13; N, 4.73.

EXAMPLE 20

3,3'-Bis[2-(1-Pyrrolidinyl)Ethoxy]Benzil

To a stirred dry suspension of 3,3'-dihydroxybenzil dithallium salt (26 g.) in toluene (1 liter) was added dropwise 40 ml. of a solution of N-(2-chloroethyl)pyrrolidine (155 g.) in toluene (500 ml.). After the mixture had been stirred and heated under reflux for ¾ hour a further 20 ml. of reagent solution and N,N-dimethylformamide (200 ml.) were added. Stirring and heating under reflux was continued for a total of 3 hours. After cooling the precipitate was collected and washed with toluene. The filtrate and washings were evaporated to a syrup which was subjected to an oil pump vacuum. The residue was extracted with chloroform and the extract was added to the top of a column (57 × 5.0 cm) of alumina (Woelm, dry-column grade) prepared in chloroform. The column was eluted with chloroform and appropriate sized fractions were collected. The fractionation was followed visually and by tlc on "ALOX-25 UV 254" plates with ethyl acetate as developer. Evaporation of the pooled fractions gave an oil which was subjected to an oil pump vacuum; yield 8.0 g. To this material dissolved in ethanol (100 ml.) was added p-toluenesulfonic acid hydrate (7.50 g.) and the solution warmed and seeded. Upon cooling 13.75 g. of crystals;(m.p. 149°–151°) was collected. Three crystallizations from methanol-ether gave pure title product as the bis(p-toluenesulfonate), hemihydrate, salt; m.p. 152-153°.

Analysis for: $C_{40}H_{48}N_2S_2O_{10}$ 0.5 $H_2O$. Calculated: C, 60.83; H, 6.25; N, 3.55; S, 8.12; $H_2O$, 1.14 %. Found: C, 60.87; H, 6.21; N, 3.55; S, 8.49; $H_2O$, 1.71.

EXAMPLE 21

The antiarrhythmic activity of the compounds of the invention is demonstrated and ellicited by the following test method:

The heart of an anesthetized dog is exposed by a left thoractomy. Bipolar electrodes are sutured to the epicardial surface of the left ventricle. The heart is stimulated with square wave pulses of 3 msec duration and frequency of 60 Hz for periods of 5 sec. Voltage is increased until fibrillation ensues. The heart is then defibrillated by DC countershock and the procedure repeated at 10 min. intervals. Drugs are administered i.v. over periods of 3 min. and fibrillatory threshold examined 10 min. after start of injection of each dose. Effective antiarrhythmic agents elevate the fibrillatory threshold.

When tested as set forth above the compounds described in the preceding examples elevate the electrical fibrillatory threshold at a dose of 5–20 mg/kg. body weight.

EXAMPLE 22

Platelet aggregation is an initial step in thrombus formation, and it is considered that compounds which prevent aggregation or reduce platelet adhesiveness inhibit one of the initiation steps of the arteriosclerotic process. The effect of drugs on aggregation is measured in platelet rich plasma (PRP) to which adenosine diphosphate (ADP), which markedly increases aggregation in vitro, is added.

Human blood is collected from fasted normal blood donors in siliconized 50 ml. Vacutainers that contain 3.8% sodium citrate. Centrifugation at 500 g. for 3 minutes at 5°C separates the red blood cells from the PRP. The supernatant PRP is pipetted off and the remainder is centrifuged at 1,000 g. for 10 minutes at 25°C to obtain platelet poor plasma for standardization of the automated Payton aggregometer. In the running of the platelet aggregation test a cell containing 1.0 ml. of PRP is stirred at 1,100 rpm and the test compound is added in 0.2 ml. of buffered saline to give an initial concentration of 5 × $10^{-4}$M. After 3 minutes, a concentration of ADP predetermined to yield marked platelet aggregation (2 to 4 $\mu$M) is added in 0.1 ml. of buffered saline. The curve of light transmission at 610 m$\mu$ is followed for 6 minutes. Compounds found to be active at the initial concentration are run at lower concentrations.

When tested as set forth above the compounds described in the preceding examples give 50% inhibition of platelet adhesiveness at a concentration of $1 \times 10^{-4}$M or less.

What is claimed is:
1. A symmetrical compound of the formula:

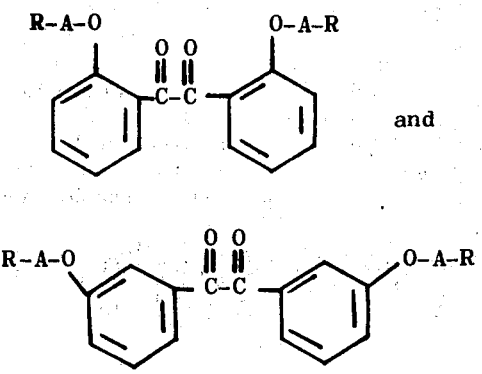

and wherein A is a divalent aliphatic hydrocarbon radical of the formula
$-CH_2CH_2-$, $-CH_2CH_2CH_2-$, or $-CH_2\overset{\underset{\displaystyle CH_3}{|}}{C}H-CH_2-$ and R is an amino group of the formula

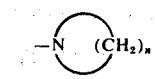

wherein n is the number 4, 5, or 6; and the non-toxic, pharmaceutically acceptable acid addition salts thereof.

2. A compound as defined in claim 1 which is 2,2'-bis-(2-piperidinoethoxy)benzil.
3. A compound as defined in claim 1 which is 2,2'-bis-(2-hexamethyleniminoethoxy)benzil.
4. A compound as defined in claim 1 which is 2,2'-bis-(3-piperidinopropoxy)benzil.
5. 2,2'-bis-[2-(3-azabicyclo[3.2.2]nonan-3-yl)ethoxy]benzil.
6. A compound as defined in claim 1 which is 2,2'-bis-(2-pyrrolidinoethoxy)benzil.
7. A compound as defined in claim 1 which is 3,3'-bis-(2-piperidinoethoxy)benzil.
8. A compound as defined in claim 1 which is 3,3'-bis-(3-piperidinopropoxy)benzil.
9. A compound as defined in claim 1 which is 3,3'-bis-(2-hexamethyleniminoethoxy)benzil.
10. 3,3'-bis-[3-(3-azabicyclo[3.2.2]nonan-3-yl)propoxy]benzil.
11. A compound as defined in claim 1 which is 3,3'-bis-(3-pyrrolidinopropoxy)benzil.
12. A compound as defined in claim 1 which is 3,3'-bis-(3-hexamethyleniminopropoxy)benzil.
13. A compound as defined in claim 1 which is 3,3'-bis-[2-(1-pyrrolidinyl)ethoxy]benzil.

* * * * *